(12) United States Patent
Hou et al.

(10) Patent No.: US 8,755,903 B2
(45) Date of Patent: Jun. 17, 2014

(54) SYSTEM OF FUNCTIONAL ELECTRICAL STIMULATION

(75) Inventors: Zengguang Hou, Beijing (CN); Min Tan, Beijing (CN); Yixiong Chen, Beijing (CN); Pengfeng Li, Beijing (CN); Hongbo Wang, Beijing (CN); Long Cheng, Beijing (CN); Guoqing Hu, Beijing (CN); Qingling Li, Beijing (CN); Feng Zhang, Beijing (CN); Jin Hu, Beijing (CN); Xinchao Zhang, Beijing (CN); Yi Hong, Beijing (CN); Junwei Zhang, Beijing (CN); Jinzhu Bai, Beijing (CN); Zhen Lv, Beijing (CN)

(73) Assignee: Institute of Automation, Chinese Academy of Sciences, Beijing (CN)

( * ) Notice: Subject to any disclaimer, the term of this patent is extended or adjusted under 35 U.S.C. 154(b) by 0 days.

(21) Appl. No.: 13/806,952

(22) PCT Filed: Jun. 28, 2011

(86) PCT No.: PCT/CN2011/076485
§ 371 (c)(1),
(2), (4) Date: Jan. 28, 2013

(87) PCT Pub. No.: WO2013/000121
PCT Pub. Date: Jan. 3, 2013

(65) Prior Publication Data
US 2013/0231724 A1 Sep. 5, 2013

(51) Int. Cl.
*A61N 1/08* (2006.01)
*A61N 1/36* (2006.01)

(52) U.S. Cl.
CPC .. *A61N 1/08* (2013.01); *A61N 1/36* (2013.01); *A61N 1/36003* (2013.01)
USPC .................................................. 607/115; 607/5

(58) Field of Classification Search
USPC ........................................................ 607/5, 115
See application file for complete search history.

(56) References Cited

FOREIGN PATENT DOCUMENTS

CN 1033443 A 6/1989
WO 2008/004204 A1 1/2008

OTHER PUBLICATIONS

International Search Report and Written Opinion (in Chinese) for PCT Application No. PCT/CN2011/076485, dated Mar. 22, 2012, 7 pages.

*Primary Examiner* — Carl H Layno
*Assistant Examiner* — Jon Eric C Morales
(74) *Attorney, Agent, or Firm* — Westman, Champlin & Koehler, P.A.

(57) ABSTRACT

The present invention discloses a functional electrical stimulation system comprising a primary power, a boost module, an energy storage section, an output control relay, an automatic discharge circuit, a foot/hand controlled switch, a current detection chip and a current limiting fuse. The boost module comprises n DC chopper circuits connected in series, and outputs a high voltage of 100-200V. According to an enable signal and a current detection signal, the output control relay disables/enables the DC boost module. The automatic discharge circuit discharges capacitance of the energy storage section automatically when the relay turns off the power input. The Foot/hand controlled switch, the current detection chip and the current limiting fuse form a triple accident protection circuit. The functional electrical stimulation system maximizes the intensity of electrical stimulation within the range that the human body can withstand. Meanwhile, it provides multiple security protection mechanisms and enhanced reliability to avoid danger during the use.

13 Claims, 2 Drawing Sheets

SYSTEM OF FUNCTIONAL ELECTRICAL STIMULATION

CROSS-REFERENCE TO RELATED APPLICATION

This application is a Section 371 National Stage Application of International Application No. PCT/CN2011/076485, filed Jun. 28, 2011, the contents of which are hereby incorporated by reference in their entirety.

TECHNICAL FIELD

The invention relates to a technical field of medical appliances, in particular to a functional electrical stimulation (FES) system.

BACKGROUND

An FES therapy uses a low-frequency current to stimulate denervated muscles, making muscle contraction in order to replace or correct functions that organs and limbs have lost. At present, research and application on FES have been involved in various fields of clinical treatment. In general, an FES device is a portable stimulator with two or four channels.

The FES can assist users with upper motor neuron injury to complete some functional activities, such as walking, grasping, and coordinated movement, which can accelerate recovery of voluntary control. Upper motor neuron injury includes cerebrovascular disease, brain trauma, spinal cord injury, cerebral palsy, etc. Limb movement is critical to the rehabilitation of these users, especially the users with spinal cord injury. The latest study found that the electrical signal, generated by the limb movement, can cause irritation on the spinal cord stump, which achieves the restoration of part of the spinal cord continuity. Some scientists have proposed a FES-assisted pedalling training method, which can restore muscle strength and promote local tissue repair of spinal cord injury.

As an important part of the FES system, a boost module provides high voltage for a stimulation output channel. Especially, when the electrical stimulation is used to generate limb movements, the boost module is required to provide higher and more stable voltage compared with the case of using the electrical stimulation for easing pain. However, output strength and load capacity of commercial electrical stimulation devices are relatively low at present. They cannot be used for the stimulation requirement of large load (for example, the electrical stimulation assists users to complete a treadmill exercise). Moreover, the security and reliability are also low. In particular, when a user uses a household electrical stimulation device without professional guidance and monitoring, the user may induces abnormal heartbeat and muscle spasm abruptly owing to electrical stimulation. It will cause secondary damage if the electrical stimulation cannot be disconnected instantly.

Thus, disadvantages of a conventional FES system may consist in:

1. The boost module cannot provide the higher and more stable electrical stimulation because of its limited boost capacity and low stimulation intensity; and
2. There is a security risk in the case of high-voltage stimulation. That is, the security and reliability are low.

SUMMARY

Technical Problems to be Solved

A functional electrical stimulation system is provided to improve intensity, security and reliability of the electrical stimulation.

Technical Solution

In accordance with an aspect of present invention, a functional electrical stimulation system comprises: a primary power; a boost module, connected with the primary power, is configured to raise an output voltage of the primary power to a first preset voltage; an energy storage module, connected with the boost module, is configured to store electrical energy of the first preset voltage; an electrical stimulation output channel, connected with the energy storage module, is configured to convert electrical energy stored in the energy storage module to a electrical stimulation pulse and apply the electrical stimulation pulse to a diseased part of a user. The boost module may comprise a timer, a voltage-regulator diode and n DC chopper circuits connected in series; the timer is configured to generate control pulses to drive the n DC chopper circuits connected in series so as to increase the output voltage to the first preset voltage in a multi-stage mode; an output of a last stage DC chopper circuit is connected to the energy storage module via a negative electrode of the voltage-regulator diode, where $n \geq 1$.

Preferably, according to present invention, the DC chopper circuit comprises a boost inductor, a transistor, a diode and a smoothing capacitor; one end of the boost inductor is connected with the primary power or an output end of a previous stage DC chopper circuit, and the other end is connected with a positive electrode of the diode; a base of the transistor is connected to an output end of the timer via a resistor R, a collector and an emitter of the transistor are connected with the positive electrode of the diode and the ground respectively. The negative electrode of the diode is connected to a next stage DC chopper circuit or the voltage-regulator diode via the smoothing capacitor.

Preferably, according to present invention, the timer is configured to provide square waves with a preset timing relationship for the base of the transistor of the n DC chopper circuits connected in series according to a preset frequency, respectively.

Preferably, according to present invention, a boost ratio of the boost module is associated with the number of the stages of the DC chopper circuits and/or duty ratios of the square waves generated by the timer.

Preferably, the functional electrical stimulation system according to present invention further comprises an automatic discharge circuit configured to release the electrical energy stored in the energy storage module when the output voltage of the primary power is lower than the first preset voltage, a control terminal of the automatic discharge circuit is connected with an output end of the primary power.

Preferably, according to present invention, the automatic discharge circuit comprises a forth transistor Q4, a fifth transistor Q5, a tenth resistor R10, a eleventh resistor R11, a twelfth resistor R12 and a thirteenth resistor R13; a base of the forth transistor Q4 is connected with a battery voltage signal via a thirteenth resistor R13, a collector of the forth transistor Q4 is connected with the energy storage module via the tenth resistor R10, and an emitter of the forth transistor Q4 is connected with the ground; a base of the fifth transistor Q5 is connected with the collector of the forth transistor Q4 via the eleventh resistor R11, a collector of the fifth transistor Q5 is connected with the energy storage module via the twelfth resistor R12, and an emitter of the fifth transistor Q5 is connected with the ground; when the output voltage of the primary power is higher than the preset voltage, the forth transistor Q4 is turned on and the fifth transistor Q5 is turned off; and when the output voltage of the primary power is lower to the preset voltage, the forth transistor Q4 is turned off and the fifth transistor Q5 is turned on so as to release the electrical energy stored in the energy storage module via the twelfth resistor R12.

Preferably, the functional electrical stimulation system according to present invention further comprises a mechanical emergency stop module having a normally open contact connected between the energy storage module and the electrical stimulation output channel; the normally open contact is turned on when the functional electrical stimulation system is in a normal mode, while the normally open contact is turned off when an emergency occurs so that a pathway between the energy storage module and the electrical stimulation output channel is disconnected. Preferably, the mechanical emergency stop module is a pressing-button switch; the normally open contact is turned on when a user is treading or pressing the switch in the normal mode; the normally open contact is turned off when the user is releasing the switch in emergency.

Preferably, the functional electrical stimulation system according to present invention further comprises a current detection chip and a current monitoring circuit; the current detection chip is connected between the energy storage module and the electrical stimulation output channel, and configured to detect a current outputted from the energy storage module; the current monitoring circuit comprises a control end connected with an output end of the current detection chip and is configured to disconnect a connection between the primary power and the boost module when a level of the current outputted from the energy storage module is higher than a preset current value. Preferably, the current monitoring circuit comprises: a comparator, a bistable flip-flop, an AND gate processor and a relay; one input end of the comparator is connected with the current detection chip, and the other input end is connected with a preset current generating device; the comparator is configured to compare the level of the current outputted from the energy storage module with the preset current value; an input end of the bistable flip-flop is connected with an output end of the comparator, an output end of the bistable flip-flop is configured as one input end of the AND gate processor; the output of the bistable flip-flop is changed from a high level to a low level when the level of the current outputted from the energy storage module is higher than the preset current value, and remains in the low level; the other input end of the AND gate processor is connected with an output enable signal, and the output end of the AND gate processor is used as a control end of the relay; the relay is configured to keep the connection between the primary power and the DC boost module when the level of the current outputted from the energy storage module is lower than the preset current value, and disconnect the connection between the primary power and the DC boost module when the level of the current outputted from the energy storage module is higher than the preset current value.

Preferably, the functional electrical stimulation system according to present invention further comprises a fuse connected between the energy storage module and the electrical stimulation output channel, the fuse is configured to disconnect the connection between the energy storage module and the electrical stimulation output channel when the level of the current outputted from the energy storage module is higher than the preset current value.

Preferably, according to present invention, setup parameters of the electrical stimulation output channel is in a range of a positive pulse width of 0-1000 μs, a negative pulse width of 0-3000 μs, a positive pulse amplitude of 0-100 mA, a negative pulse amplitude of 0-50 mA and a pulse frequency of 0-100 Hz.

Preferably, according to present invention, the primary power is a battery; the boost module is a DC boost module; and the energy storage module is a storage capacitor.

Technical Effect

The functional electrical stimulation system according to present invention has at least following advantages of:
1) providing a higher and more stable high voltage compared with the conventional system and increasing the intensity of electrical stimulation effectively.
2) employing security measures to improve the security and reliability. And avoiding secondary damage caused by FES, such as abnormal heart beat and muscle spasm effectively.

DETAILED DESCRIPTION

To make the purpose, technical scheme and advantages of present invention clear, a more detailed explanation for this invention is given by embodiments with reference to the drawings.

It should be noted that, in order to avoid confusing the information data signal connection (weak signal) with the functional electrical signal connection (strong signal), the embodiment just relates to the connection relationship of the functional electrical signal, and the connection relationship of the information data signal will only be described with the flow of the information data signal. In the present embodiment and each of the following embodiments, most of the components are not provided with the specific model and value except some special components that are different from the prior art. The applicant believes that those skilled in the art can select the specific model and value of the components after becoming aware of the above technical solutions. It should certainly within the scope of the present invention.

Figure 1:
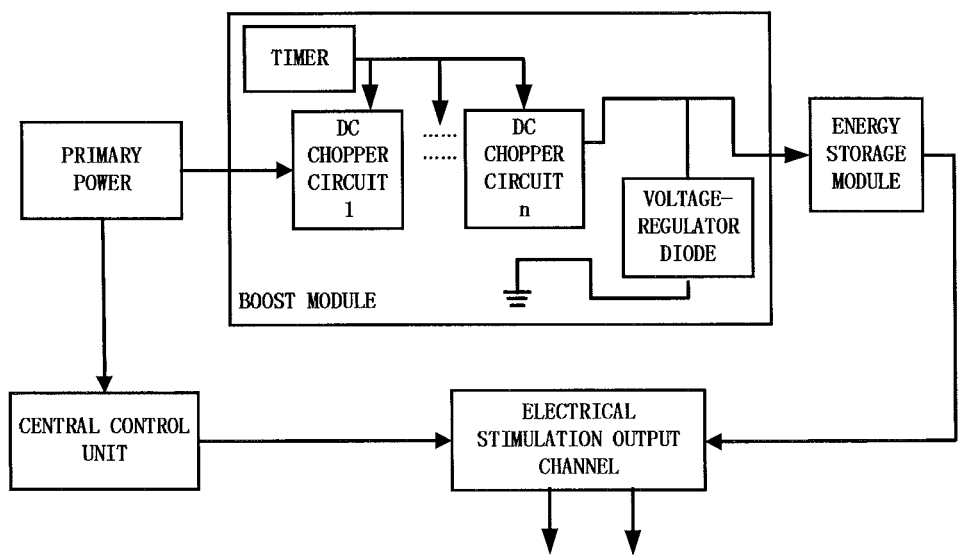
FIG. 1 shows a structure diagram of a functional electrical stimulation system according to an embodiment of present invention.

A functional electrical stimulation system according to an exemplary embodiment of the present invention is provided. FIG. 1 is a structure diagram of the functional electrical stimulation system. As shown in FIG. 1, the functional electrical stimulation system according to the exemplary embodiment of the present invention may include: a primary power; a boost module connected with the primary power, and is configured to raise an output voltage of the primary power to a first preset voltage; an energy storage module connected with the boost module, and is configured to store an electrical energy of the first preset voltage; an electrical stimulation output channel connected with the energy storage module, and is configured to convert the electrical energy stored in the energy storage module to an electrical stimulation pulse and apply the electrical stimulation pulse to a diseased part of a user. The boost module may include a timer, a voltage-regulator diode and n DC chopper circuits connected in series. The timer generates control pulses to drive the n DC chopper circuits connected in series so as to increase the output voltage to the first preset voltage in a multi-stage mode. An output of a last stage DC chopper circuit is connected to the energy storage module via a negative electrode of the voltage-regulator diode, where n≥1.

Preferably, according to the embodiment of the invention, the primary power may be a battery, the boost module may be a DC boost module, and the energy storage module may be a storage capacitor. Setup parameters of the electrical stimulation output channel may be set in a range of: a positive pulse width of 0-1000 μs, a negative pulse width of 0-3000 μs, a positive pulse amplitude of 0-100 mA), a negative pulse amplitude of 0-50 mA and a pulse frequency of 0-100 Hz.

The conventional functional electrical stimulation system cannot provide a higher and more stable electrical stimulation due to the limited boost capacity and low stimulation intensity. To solve this problem, the boost module in the present invention can increase voltage via the DC chopper circuit in the multi-stage mode. The stage number of the DC chopper circuits can be set as needed. Preferably, n=2, 3, 4, 5 or 6.

Figure 2:
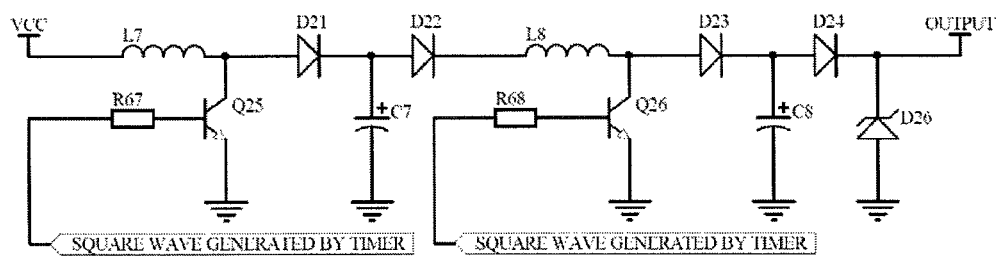
FIG. 2 is a schematic diagram of a boost module in the functional electrical stimulation system according to an embodiment of present invention.

FIG. 2 is a schematic diagram of the boost module in the functional electrical stimulation system. As shown in FIG. 2, the DC chopper circuit may include a boost inductor, a transistor A44, a diode 1N4007 and a smoothing capacitor. One end of the boost inductor is connected with the primary power or an output end of a previous stage DC chopper circuit, and the other end is connected with the positive electrode of the diode. A base of the transistor is connected to an output end of the timer via a resistor R. In addition, a collector and an emitter of the transistor are connected with a positive electrode of the diode and the ground respectively. The negative electrode of the diode is connected to a next stage DC chopper circuit or the voltage-regulator diode via the smoothing capacitor. The timer provides square waves with the preset timing relationship respectively for the base of the transistor of the n DC chopper circuits connected in series according to a preset frequency.

According to the embodiment of the invention, a boost ratio of the boost module may be associated with the stage number of the DC chopper circuits and/or a duty ratio of square wave generated by the timer. A theoretical formula for the boost module is:

$$V_{out} = V_{in} \times (1/(1-D))^n \quad (1)$$

Where D is a duty ratio of the square wave pulse; n is the stage number of the DC chopper circuits; $V_{in}$ is an initial input voltage of the boost module; $V_{out}$ is an output voltage of the boost module. It should be noted that an actual output voltage may be varied greatly from the theoretical formula. Those skilled in the art may set the parameters according to an actual scene.

Preferably, according to the embodiment of the invention, the timer may be integrated in a controller, or implemented with a dedicated timing chip. A pulse frequency of the timer may be set in a range from 1 Khz to 100 Khz.

It should be noted that the embodiment only provides an example of the DC chopper circuit, and those skilled in the art may envision other implementations of the DC chopper circuit from the disclosure, such as using an MOSFET to replace the transistor or using an analog switch to replace the diode, which fall into the scope of the present invention. In addition, the boost module also may be realized by using a boosting transformer to increase the power voltage to a necessary AC high voltage and then convert the AC high voltage to a DC high voltage via a rectifier circuit or to a desired target voltage via multiple isolated DC/DC modules in series.

Preferably, according to the embodiment of the invention, the functional electrical stimulation system may additional include an automatic discharge circuit. A control terminal of the automatic discharge circuit is connected with the output end of the primary power so as to release the electrical energy stored in the energy storage module when the voltage of the primary power is lower than the first preset voltage.

Figure 3:
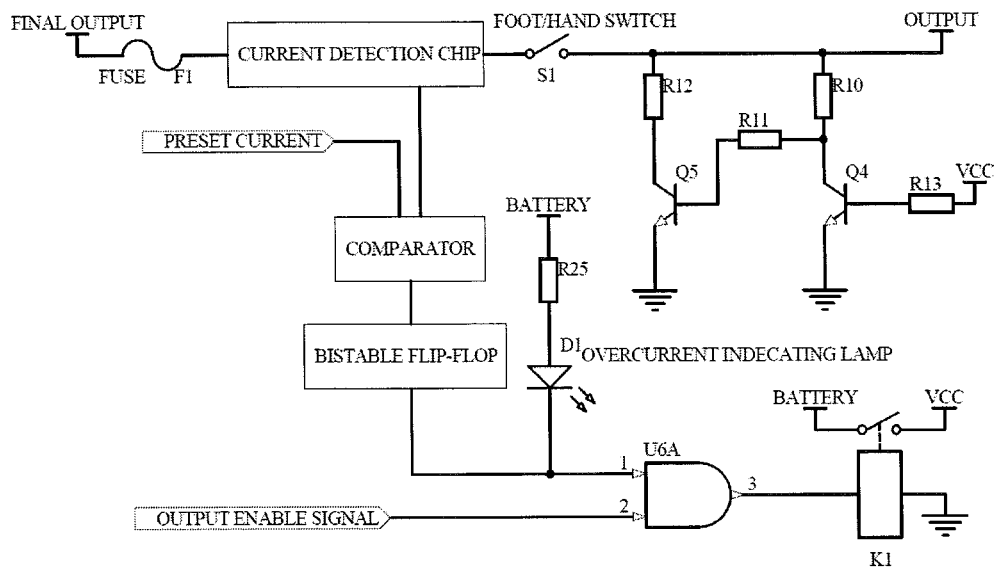
FIG. 3 is a schematic diagram of a peripheral circuit in the functional electrical stimulation system according to an embodiment of present invention.

FIG. 3 is the schematic diagram of a peripheral circuit in the functional electrical stimulation system. As shown in FIG. 3, the automatic discharge circuit may include: a transistor Q4, a transistor Q5, a resistor R10, a resistor R11, a resistor R12, and a resistor R13. A base of the transistor Q4 is connected with a battery voltage signal via the resistor R13, a collector of the transistor Q4 is connected with the energy storage module via the resistor R10, and an emitter is connected with the ground. A base of the transistor Q5 is connected with the collector of the transistor Q4 via the resistor R11, a collector of the transistor Q5 is connected with the energy storage module via the resistor R12, and an emitter is connected with the ground. When the voltage of the primary power is higher than a preset voltage, the transistor Q4 is turned on and the transistor Q5 is turned off; and when the voltage of the primary power is lower than the preset voltage, the transistor Q4 is turned off and the transistor Q5 is turned on so that the electrical energy stored in the energy storage module is released via the resistor R12.

According to the embodiment of the present invention, the high voltage generated by the boost module is stored in an electrolytic capacitor with large capacity. The energy in the capacitor need to be released rapidly when the boost module stops output or is powered off unexpectedly so as to avoid an accident due to long time storage of the energy.

In order to ensure the user's safety, a triple accident protection circuit is formed with a foot/hand controlled switch, a current detection chip and a current limiting fuse according to the embodiment.

A first part is an emergency stop protection device including the foot/hand controlled switch. This emergency stop protection device allows the user to break away from the stimulation immediately when the user induces abnormal heart beat or muscle spasm caused by the electrical stimulation. As shown in FIG. 3, the emergency stop protection device is connected in series in a high-voltage output loop (for example, between the energy storage module and the electrical stimulation output channel) so as to output the high voltage only when the user treads/presses the switch. The user can loosen the switch to disconnect the high voltage output in case that any unexpected circumstances are occurred. In addition, the emergency stop protection device allows the user to feel that they can disconnect the electrical stimulation at all times so as to alleviate a risk caused by the electrical stimulation therapy and improve treatment effect.

A second part is a current monitoring circuit including the current detection chip. The current monitoring circuit allows the relay to disconnect the power supply of DC boost module when an average value of the output current exceeds a set value such as 10 mA. Specifically, the functional electrical stimulation system may include the current detection chip and the current monitoring circuit. The current detection chip is connected between the energy storage module and the electrical stimulation output channel to detect a current outputted from the energy storage module. The current monitoring circuit has a control end connected with the output end of the current detection chip and is configured to disconnect the connection between the primary power and the boost module when the level of the output current of the energy storage module is higher than a preset current value.

As shown in FIG. 3, the current monitoring circuit may include a comparator, a bistable flip-flop, an AND gate processor and a relay. One input end of the comparator is connected with the current detection chip, and the other input end is connected with a device for generating a preset current. The comparator is configured to compare a level of the current outputted from the energy storage module with a preset current value. An input end of the bistable flip-flop is connected with an output end of the comparator, and an output end is used as one input end of the AND gate processor so as to change a state of bistable flip-flop from high level to low when the level of the current outputted from the energy storage module is higher than the preset current value, and remain the level in a low state. The other input end of the AND gate processor is connected with an output enable signal, and the output end of the AND gate is used as a control end of the relay. The relay keeps a connection between the primary power and the DC boost module when the level of the current outputted from the energy storage module is lower than the preset current value; and the connection between the primary power and the DC boost module is disconnected when the level of the current outputted from the energy storage module is higher than the preset current value. The output enable signal is used for enabling a normal output of the functional electrical stimulation system, and is provided by the host controller.

The third part is the current limiting fuse which is connected in series in the high-voltage output loop. As shown in FIG. 3, the FES belongs to a pulse stimulation with a small duty ratio so that the average current is less than a body safety current of 10 mA. Although the peak value of current can reach to 100 mA, a 32 mA (rather than 100 mA) fast-blow fuse can be used to protect the user security. The fuse can blow out rapidly when the current flows through human body constantly due to a system failure.

According to the embodiment of the present invention, the functional electrical stimulation system increases the security so as to alleviate the user's risk during the normal use. In addition, a secondary damage caused by the FES, such as abnormal heart beat and muscle spasm, can be avoided effectively.

A preferable embodiment of the present invention will be described on the basis of the above embodiment. It should be noted that this preferable embodiment is only for understanding of the present invention, and is not intended to limit the scope of the present invention. Further, features of the preferable embodiment are all applicable to the embodiment of the respective devices unless context dictates otherwise. It will be readily understood that the aspects of the present disclosure, as generally described herein, and illustrated in the Figures, can be arranged, substituted, combined, and designed in a wide variety of different configurations, all of which are explicitly contemplated and are made part of this disclosure.

Figure 4:
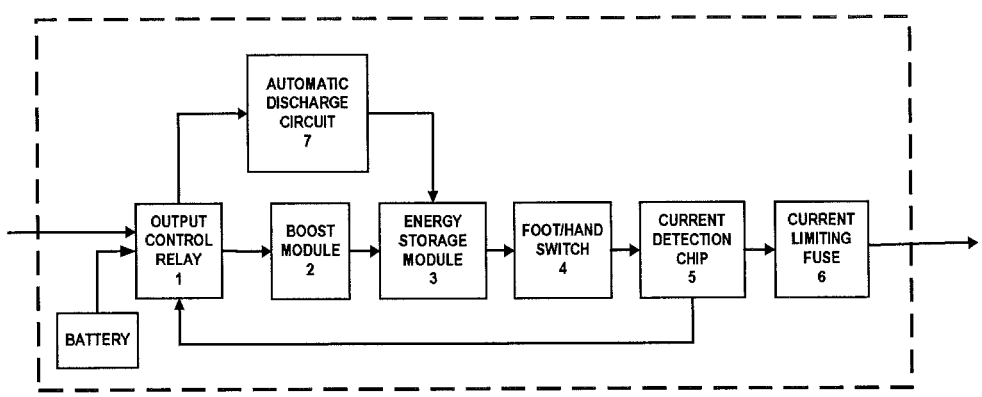
FIG. 4 is a block diagram of the functional electrical stimulation system according to an embodiment of present invention.

FIG. 4 is a block diagram of the functional electrical stimulation system according to present invention. As shown in FIG. 4, the functional electrical stimulation system may include an output control relay 1, a DC boost module 2, an energy storage module 3, a foot/hand controlled switch 4, a current detection chip 5, a current limiting fuse 6, and an automatic discharge circuit 7.

The DC boost module 2 shown in FIG. 4 is a relatively important part in the whole system. This module is configured to raise the battery voltage to the high voltage for the electrical stimulation. The DC boost module 2 may include two DC chopper circuits connected in series. With reference to FIG. 2, a 555 timer generates a square signal of 50 KHz to drive transistors Q25 and Q26. The current flows through inductors L7 and L8 when the transistors Q25 and Q26 are turned on. Diodes prevent capacitors C7 and C8 from discharging to ground. C7 and C8 may be 10 μF electrolytic capacitors with 400V high-voltage resistance. With increasing of the inductor current, electric energy in L7 and L8 is stored in a form of magnetic energy. Due to a holding characteristic of inductor current, the inductor generates a reverse potential when the transistor is turned off. Since the energy cannot discharge through the off transistor, this potential is superimposed on an original potential of capacitor for boosting. In addition, the DC boost module with a single stage is not enough to generate a stable high voltage that meets design requirements, thus the module may be implemented in a two-stage mode in series to increase voltage. A final output voltage is determined by a voltage-regulator diode D26 and the duty ratio of the square signal generated by the 555 timer. The range of output voltage may be 100-200V.

The high voltage generated by the DC boost module is stored in the electrolytic capacitor with large capacity. The energy in the capacitor need to release rapidly when the boost module stops output or is powered off unexpectedly so as to avoid an accident due to long time storage of the energy. This function may be achieved by the automatic discharge circuit. With reference to FIG. 3, a relay K1 is in a closed state normally. VCC is the battery voltage which may be 12V. Q4 is in turn-on state. A turn-on voltage (about 0.2V) at a collector of Q4 is not enough to turn on Q5. R10 is a high-impedance resistance with only 0.1 μA current flowing through and no discharge may be caused. When the battery voltage signal is disconnected due to powering off, Q4 is in the off state, the voltage at the collector of Q4 is pulled up to 100-200V so as to turn on Q5 and the stored energy is released through the ground loop established by R12.

The triple accident protection circuit may include the foot/hand controlled switch, the current detection chip and the current limiting fuse. The primary protection mechanism may be implemented with the foot/hand controlled switch S1 in FIG. 3. The user controls this switch and he/she can select the switch type according to an action part of FES. A hand-held mechanical emergency stop switch is used if for electrical stimulation of lower limb. Similarly a tread-type switch is used for electrical stimulation of upper limb. A normally open contact of foot/hand controlled switch is connected in series in the DC boost output loop. A normally closed contact is connected with an LED indicator lamp. When the user treads/presses the switch during the normal use, the normally open contact turns on to output the high voltage. The normally closed contact is in the off state and the LED indicator lamp is turned off. When the user releases the switch when an emergency occurs, the normally open contact is turned off to avoid the high-voltage output, thus the electrical stimulation is turned off. The normally closed contact is in a turn-on state, so that the LED indicator lamp turns on to generate an alert signal.

The secondary protection mechanism may be implemented with the current monitoring circuit including the current detection chip and the related components shown in FIG.

3. The current detection chip is connected in series in the high-voltage output loop and generates an analog voltage signal with a level linear to a average value of the output current value. Then the analog voltage signal is compared by a comparator with the analog voltage signal corresponding to 10 mA, so as to determine whether the average of output current value exceeds 10 mA or not. If so, the state of bistable flip-flop is changed from high level to low, an AND operation is applied on the low level and the output-enable signal by U6 (AND gate) to obtain a result in low level. Then the relay K1 disconnects, so that the high-voltage output is stopped due to lacking the power supply for the DC boost module. Meanwhile the indicator lamp D1 turns on to alert the user that the output current is too excessive. The output level of bistable flip-flop keeps in the low state due to its memory characteristic and the relay is not closed again.

An inrush current caused by unpredicted circumstances is possible to harm the user before the action of the previous dual protection mechanisms. Therefore, the third protection mechanism may be implemented with the fuse F1 in FIG. 3 to protect the user security. F1 is a 32 mA fast-blow fuse. The FES belongs to the pulse stimulation with the small duty ratio and the average current (below 1-2 mA) is less than the body safety current. Therefore although a peak value of output current may be 100 mA, the fuse does not blow out in normal operation. When an excessive current flows through human body constantly due to the system failure, the fuse may be blow out rapidly to protect the user security. As known in the art, only when the average current flowing through the human body is greater than 90-100 mA, will the human appear the symptom of respiratory paralysis, when the excessive current lasts around 3 min or longer, the heart will attack or stop beating, and when the average current flowing through the human body is 20-40 mA, the human will feel pain in fingers, increased burning sensation and spasm in the hand muscles and the like. This will not cause a life-threatening condition instantly. Therefore, it has adequate safety allowance to select the fuse with 32 mA of fusing current.

In general, the functional electrical stimulation system according to present invention can maximize the intensity of electrical stimulation within the range that the human body can withstand. Meanwhile, it provides multiple security protection mechanisms and the enhanced reliability to avoid danger during the use.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A functional electrical stimulation system comprising:
   a primary power;
   a boost module connected with the primary power, and is configured to raise an output voltage of the primary power to a first preset voltage;
   an energy storage module connected with the boost module, and is configured to store electrical energy of the first preset voltage; and
   an electrical stimulation output channel connected with the energy storage module, and is configured to convert the electrical energy stored in the energy storage module to an electrical stimulation pulse and apply the electrical stimulation pulse to a diseased part of a user;
   wherein the boost module comprises a timer, a voltage-regulator diode and n DC chopper circuits connected in series; the timer is configured to generate control pulses to drive the n DC chopper circuits connected in series so as to increase the output voltage to the first preset voltage in a multi-stage mode; an output of a last stage DC chopper circuit is connected to the energy storage module via a negative electrode of the voltage-regulator diode, where n≥1.

2. The functional electrical stimulation system according to claim 1, wherein the DC chopper circuit comprises a boost inductor, a transistor, a diode and a smoothing capacitor;
   one end of the boost inductor is connected with the primary power or an output end of a previous stage DC chopper circuit, and other end is connected with a positive electrode of the diode;
   a base of the transistor is connected to an output end of the timer via a resistor R, a collector and an emitter of the transistor are connected with the positive electrode of the diode and a ground respectively;
   a negative electrode of the diode is connected to a next stage DC chopper circuit or the voltage-regulator diode via the smoothing capacitor.

3. The functional electrical stimulation system according to claim 2, wherein the timer is configured to provide square waves with a preset timing relationship for the base of the transistor of the n DC chopper circuits connected in series according to a preset frequency, respectively.

4. The functional electrical stimulation system according to claim 3, wherein a boost ratio of the boost module is associated with the number of the stages of the DC chopper circuits and/or duty ratios of the square waves generated by the timer.

5. The functional electrical stimulation system according to claim 1, further comprising an automatic discharge circuit configured to release the electrical energy stored in the energy storage module when the output voltage of the primary power is lower than the first preset voltage; a control terminal of the automatic discharge circuit is connected with an output end of the primary power.

6. The functional electrical stimulation system according to claim 5, wherein the automatic discharge circuit comprises a forth transistor (Q4), a fifth transistor (Q5), a tenth resistor (R10), a eleventh resistor (R11), a twelfth resistor (R12) and a thirteenth resistor (R13);
   a base of the forth transistor (Q4) is connected with a battery voltage signal via a thirteenth resistor (R13), a collector of the forth transistor (Q4) is connected with the energy storage module via the tenth resistor (R10), and an emitter of the forth transistor (Q4) is connected with the ground;
   a base of the fifth transistor (Q5) is connected with the collector of the forth transistor (Q4) via the eleventh resistor (R11), a collector of the fifth transistor (Q5) is connected with the energy storage module via the twelfth resistor (R12), and an emitter of the fifth transistor (Q5) is connected with the ground;
   when the output voltage of the primary power is higher than the preset voltage, the forth transistor (Q4) is turned on and the fifth transistor (Q5) is turned off; and when the output voltage of the primary power is lower to the preset voltage, the forth transistor (Q4) is turned off and the fifth transistor (Q5) is turned on so as to release the electrical energy stored in the energy storage module via the twelfth resistor (R12).

7. The functional electrical stimulation system according to claim 1, further comprising a mechanical emergency stop module having a normally open contact connected between the energy storage module and the electrical stimulation output channel;

the normally open contact is turned on when the functional electrical stimulation system is in a normal mode, while the normally open contact is turned off when an emergency occurs so that a pathway between the energy storage module and the electrical stimulation output channel is disconnected.

8. The functional electrical stimulation system according to claim 7, wherein the mechanical emergency stop module is a pressing-button switch; the normally open contact is turned on when a user is holding or pressing the switch in the normal mode; the normally open contact is turned off when the user is releasing the switch when the emergency occurs.

9. The functional electrical stimulation system according to claim 7, further comprising a current detection chip and a current monitoring circuit; wherein
the current detection chip is connected between the energy storage module and the electrical stimulation output channel, and configured to detect a current outputted from the energy storage module;
the current monitoring circuit comprises a control end connected with an output end of the current detection chip and configured to disconnect a connection between the primary power and the boost module when a level of the current outputted from the energy storage module is higher than a preset current value.

10. The functional electrical stimulation system according to claim 9, wherein the current monitoring circuit comprises: a comparator, a bistable flip-flop, an AND gate processor and a relay;
one input end of the comparator is connected with the current detection chip, and the other input end is connected with a preset current generating device; the comparator is configured to compare the level of the current outputted from the energy storage module with the preset current value;
an input end of the bistable flip-flop is connected with an output end of the comparator, an output end of the bistable flip-flop is configured as one input end of the AND gate processor; the output of the bistable flip-flop is changed from a high level to a low level when the level of the current outputted from the energy storage module is higher than the preset current value, and remains in the low level;
other input end of the AND gate processor is connected with an output enable signal, and the output end of the AND gate processor is used as a control end of the relay; and
the relay is configured to keep the connection between the primary power and the DC boost module when the level of the current outputted from the energy storage module is lower than the preset current value, and disconnect the connection between the primary power and the DC boost module when the level of the current outputted from the energy storage module is higher than the preset current value.

11. The functional electrical stimulation system according to claim 9, further comprising a fuse connected between the energy storage module and the electrical stimulation output channel, the fuse is configured to disconnect the connection between the energy storage module and the electrical stimulation output channel when the level of the current outputted from the energy storage module is higher than the preset current value.

12. The functional electrical stimulation system according to claim 1, parameters of the electrical stimulation output channel is set in a range of a positive pulse width of 0-1000 μs, a negative pulse width of 0-3000 μs, a positive pulse amplitude of 0-100 mA, a negative pulse amplitude 0-50 mA and a pulse frequency of 0-100 Hz.

13. The functional electrical stimulation system according to claim 1, the primary power is a battery; the boost module is a DC boost module; and the energy storage module is a storage capacitor.

* * * * *